(12) United States Patent
Lee

(10) Patent No.: US 8,075,449 B2
(45) Date of Patent: Dec. 13, 2011

(54) APPARATUS AND METHOD FOR LOWER-LIMB REHABILITATION TRAINING USING WEIGHT LOAD AND JOINT ANGLE AS VARIABLES

(75) Inventor: Yang-Soo Lee, Daegu (KR)

(73) Assignee: Industry-Academic Cooperation Foundation, Kyungpook National University, Daegu (KR)

( * ) Notice: Subject to any disclaimer, the term of this patent is extended or adjusted under 35 U.S.C. 154(b) by 288 days.

(21) Appl. No.: 11/387,396

(22) Filed: Mar. 23, 2006

(65) Prior Publication Data

US 2006/0217233 A1 Sep. 28, 2006

(30) Foreign Application Priority Data

Mar. 24, 2005 (KR) ........................ 10-2005-0024333

(51) Int. Cl.
*A63B 71/00* (2006.01)
*A63B 23/08* (2006.01)
*A63B 23/10* (2006.01)
*A63F 9/24* (2006.01)
*A63F 13/00* (2006.01)
*G06F 17/00* (2006.01)
*G06F 19/00* (2006.01)
*A61B 5/103* (2006.01)
*A61B 5/117* (2006.01)

(52) U.S. Cl. .................... 482/8; 482/79; 463/7; 463/36; 600/595

(58) Field of Classification Search .................. 600/587, 600/595; 482/8, 9, 79; 463/9–11, 36–39; 434/258
See application file for complete search history.

(56) References Cited

U.S. PATENT DOCUMENTS

| 4,745,930 A | * | 5/1988 | Confer ........................ 600/595 |
| 4,813,436 A | * | 3/1989 | Au ................................ 600/595 |
| 4,850,591 A | * | 7/1989 | Takezawa et al. .............. 463/37 |
| 5,229,756 A | * | 7/1993 | Kosugi et al. ................. 345/156 |
| 6,190,287 B1 | * | 2/2001 | Nashner ........................... 482/8 |
| 6,413,190 B1 | * | 7/2002 | Wood et al. ................... 600/505 |
| 6,909,420 B1 | * | 6/2005 | Nicolas et al. ................ 345/156 |

* cited by examiner

*Primary Examiner* — Max Hindenburg
*Assistant Examiner* — John Pani
(74) *Attorney, Agent, or Firm* — Husch Blackwell LLP

(57) ABSTRACT

The present invention relates to an apparatus and method for lower-limb rehabilitation training of a patient with lower limb paralysis. The invention measures the usage of the paralyzed lower limb, and based upon the measurement, forces patients with lower limb paralysis to use partially paralyzed muscles which they are not likely to use. The apparatus can measure the weight load and the angle of the joint, and by using the measure values as variables, display the condition of paralysis to the patient so that he/she can recognize his/her present condition of paralysis, and enable the user to training through feedback. The joint includes all of knee joint, ankle joint and hip joint of the lower limb, and the movement of important muscles of the lower limb can be detected. With the apparatus attached, the patient can perform a balance training of alternatively raising the paralyzed lower limb and the normal limb, a standing training of bending and straightening both knees of the lower limbs and a walking training of using the both lower limbs.

4 Claims, 15 Drawing Sheets

APPARATUS AND METHOD FOR LOWER-LIMB REHABILITATION TRAINING USING WEIGHT LOAD AND JOINT ANGLE AS VARIABLES

CLAIM OF PRIORITY

This application makes reference to and claims all benefits accruing under 35 U.S.C. §119 from an application for "APPARATUS AND METHOD FOR LOWER-LIMB REHABILITATION TRAINING USING WEIGHT LOAD AND JOINT ANGLE AS VARIABLES" earlier filed in the Korean Intellectual Property Office on Mar. 24, 2005 and there duly assigned Serial No. 2005-24333.

BACKGROUND OF THE INVENTION

1. Field of the Invention

The present invention relates to an apparatus and method for lower-limb rehabilitation training of a patient with a paralyzed lower limb (hereinafter will be referred to "patient with lower-limb partial paralysis"). Particularly, the apparatus for lower-limb rehabilitation training of the invention can measure changes in the weight loaded on the lower limb and in the angle of a joint while using the changes in the weight and the joint angle as variables in order to measure the condition of paralysis of the lower limb. In addition, the apparatus of the invention can display the condition of paralysis to the patient with lower-limb paralysis in various ways so that the patient can recognize the usage of the lower limb and make efforts to improve its usage, thereby making feedback effects. Furthermore, by using the rehabilitation training apparatus, the patient can alternatively raise the heels, bend the knees or walk as rehabilitation training.

2. Description of the Related Art

Hemiplegia or partial paralysis (hereinafter will be referred to as "partial paralysis") originating from apoplexy, traumatic brain damage or cerebral palsy is a motor paralysis that paralyzes muscles or motors so that the paralyzed muscles cannot exert power to a proper extent at necessary moments. In order to treat the patient with partial paralysis, it is possible to use several methods such as physical strengthening, muscle controlling, stretching, balancing and so on. As a rehabilitation training of the patient with upper-limb partial paralysis, a treatment for forcing the patient to use the paralyzed upper limb is being recognized as the most successful among several rehabilitation trainings.

A conventional treatment apparatus for enabling forced use of a paralyzed lower limb is disclosed in for example Korean Patent Application No. 1997-0028382, titled "A Rehabilitation Training System for Balancing a Posture." As shown in FIG. 1, the system for enabling forced use of the paralyzed lower limb in the document of "A Rehabilitation Training System for Balancing a Posture" includes a part 11 for measuring weight loaded on both lower limbs and a part 12 for notifying measurement values to the user so that the user can compare on which one of the both lower limbs weight is loaded more. However, the prior art of "A Rehabilitation Training System for Balancing a Posture" considers shifting the center of weight only, but does not consider the angle of a joint. Accordingly, even though the prior art has symmetrically distributed weight, walking ability has not been improved.

In practice, in case of normal walking, one bears the weight on one lower limb with its knee bent for about 15° while raising the other lower limb. Then, the knee of the lower limb supporting the weight is straightened and the weight center of the other lower limb is shifted forward. It is carried out repeatedly. As the normal walking is carried out through the shift of weight center as well as change in the angle of the lower limb, the angle of the joint is an important variable of walking. As illustrated with the normal walking, the shift of the weight center together with change in the angle of the joint enables the movement of the lower limb.

However, a patient with lower-limb partial paralysis has trouble in bending the knee owing to paralysis, and thus tends to shift the center of weight without bending the knee. This results in abnormal walking of the patient.

Accordingly, it should be confirmed whether or not the weight is loaded evenly onto both lower limbs and the joint is systematically working along with the weight load in order that the rehabilitation training system or apparatus for lower-limb partial paralysis can be more effectively used in balance and walking trainings.

Examples of the apparatus for measuring the joint is systematically working along with the weight. Since the three-dimensional walking analysis system three dimensionally analyzes images taken by the three cameras 21 or more, analysis process is complicated and too time-consuming to enable real-time feedback. Furthermore, since the force plate 22 needs a wide place, this system also disadvantageously needs a large space and expensive equipments. Therefore, the three-dimensional walking analysis system is not used for walking training.

Accordingly, there are needs for an apparatus and method for rehabilitation training that can be constituted of inexpensive equipments to measure the weight load and changes in the joint angle while displaying the measurement in real-time to the user.

SUMMARY OF THE INVENTION

The present invention has been made to solve the foregoing problems of the prior art and it is therefore an object of the present invention to provide an apparatus and method for lower-limb rehabilitation training that can measure the weight load and the angle of the joint to determine the usage of the paralyzed lower limb thereby enabling lower-limb rehabilitation training based upon the determined usage of the paralyzed lower limb.

It is another object of the invention to provide an apparatus and method for lower-limb rehabilitation training that can measure the angle of at least one of the knee joint, the ankle joint and the hip joint (i.e., coax) of the lower limb to detect the usage of the paralyzed muscles thereby enabling rehabilitation training for the paralyzed muscles based upon measurement data.

It is other object of the invention to provide an apparatus and method for lower-limb rehabilitation training that can measure the usage of the normal lower limb of a patient with lower-limb partial paralysis to use as reference in measuring the usage of paralyzed muscle or to use normal person's data stored in the apparatus in order to enable normal walking training.

It is further another object of the invention to provide an apparatus and method for lower-limb rehabilitation training using the weight load and the angle of the joint that can two-dimensionally measure the movement of the joint to rapidly analyze and display the condition of paralysis in order to enable feedback through a process in which the user recognizes his/her condition and endeavors to improve the condition. Furthermore, it is another object of the invention to constitute the apparatus for lower limb rehabilitation training with inexpensive equipments through two-dimensional measurement of the movement of the joint.

Furthermore, it is yet another object of the invention to provide a method for lower limb rehabilitation training that can measure and analyze the usage of the paralyzed muscle of a user who repeatedly carries out task actions with the apparatus for lower limb rehabilitation training attached thereto so that user can carry out training based upon the measurement and analysis so as to improve the usage of the paralyzed muscle.

In order to realize the above objects, the invention provides an apparatus for lower-limb rehabilitation training which uses weight load and joint angle, comprising: a weight-measuring part placed to contact a bottom of a lower limb, the weight-measuring part measuring weight loaded on the lower limb to generate weight data; a joint angle-measuring part for measuring the angle of a joint of the lower limb to generate joint angle data; a controller for generating result data from the weight data measured by the weight-measuring part, the joint angle data measured by the joint angle-measuring part and weight data and joint angle data of reference data; and a display part for displaying the result data generated by the controller to a user.

Preferably, the joint angle-measuring part may include at least one selected from a group consisting of a knee joint angle-measuring part for measuring the angle of a knee joint to detect whether or not the user moves by using thigh muscles, an ankle joint angle-measuring part for measuring the angle of an ankle joint to detect whether or not the user moves by using calf muscles and a hip joint angle-measuring part for measuring the angle of a hip joint to detect the degree of force for raising the leg. More preferably, the joint angle-measuring part may include all of the knee joint angle-measuring part, the ankle joint angle-measuring part and the hip joint angle-measuring part in order to synthetically measure whether or not the lower limb is moved by using major muscles of the lower limb including the thigh muscles and the calf muscles and whether or not there is force for raising the lower limb.

Preferably, the controller may generate time data of measurement data from a time period counted until the weight data measured by the weight-measuring part becomes substantially the same and time comparison data from the difference between the time data of the measurement data and reference time data. Also, the controller may generate measurement data including the weight data generated by the weight-measuring part and joint angle data generated by the joint angle-measuring part simultaneously with the weight data, to generate weight comparison data and joint angle comparison data through the measurement data and the reference data each including the weight data and the joint angle data, and to generate condition data through the weight comparison data and the joint angle comparison data.

Preferably, the joint angle comparison data includes at least one of selected from a group consisting of knee joint angle comparison data, ankle joint angle comparison data and hip joint angle comparison data, wherein the knee joint angle comparison data is generated through knee joint angle data of the measurement data generated by a knee joint angle-measuring part and knee joint angle data of the reference data, wherein the ankle joint comparison data is generated through ankle joint angle data of the measurement data generated by the ankle joint angle-measuring part and ankle joint angle data of the reference data, and wherein the hip joint angle comparison data is generated through hip joint angle data of the measurement data generated by the hip joint angle-measuring part and hip joint angle data of the reference data.

Preferably, the result data includes at least one selected from a group consisting of time data, weight data and joint angle data of the measurement data; time data, weight data and joint angle data of the reference data; and time comparison data, weight comparison data, joint angle comparison data and condition data.

Also, the reference data is preferably generated by measuring a normal one of both lower limbs or previously storing normal person's data.

Preferably, the controller may generate a game by using the result data as parameters in order to get the user interested in training, wherein the game is operated so that the object of the game is accomplished when weight comparison data is within an error range and joint angle comparison data is within an error range.

Preferably, the display part may display at least one selected from a group consisting of a weight data graph of the measurement and reference data generated in real-time with time on one axis and the weight data on the other axis, a knee joint angle data graph of the measurement and reference data generated in real-time with time on one axis and knee joint angle data on the other axis, an ankle joint angle data graph of the measurement and reference data generated in real-time with time on one axis and ankle joint angle data on the other axis, a hip joint angle data graph of the measurement and reference data generated in real-time with time on one axis and hip joint angle data on the other axis, and a condition data graph with time one axis and condition data on the other axis, the condition data generated in real-time through weight comparison data and joint angle comparison data in order to assist the user to easily recognize conditions.

Preferably, the display part may display at least one selected from a group consisting of weight comparison data, angle comparison data, condition data and time comparison data with numbers or characters in order to assist the user to easily recognize conditions.

Preferably, the weight-measuring part may comprise a force plate including at least one pressure sensor positioned in contact with disposed at a position contacting a bottom of the lower limb in order to measure weight loaded on the lower limb based upon variation in the pressure sensor, or comprise at least one balance including a spring placed to directly or indirectly contact a bottom of the lower limb to be deformed under the weight loaded on the lower limb in order to measure the weight loaded on the lower limb based upon the deformation of the spring.

Preferably, the joint angle-measuring part may comprise an electric goniometer including a flexible bar capable of bending along with a joint and an attachment support connected to upper and lower regions of the joint and to the flexible bar for fixing the flexible bar aside the joint, the goniometer capable of measuring the angle of the joint based upon the degree of bending of the flexible bar. Alternatively, the joint angle-measuring part may comprise a variable resistance goniometer including a variable resistor capable of varying resistance value in response to variation in the angle of the joint, the variable resistor having a resistance adjusting part positioned to move along with the joint, and an attachment support attached to upper and lower regions of the joint to fix the variable resistor, or a motion capturing goniometer including a camera and a patch attachable to a joint and upper and lower regions of the joint and recognizable by the camera, the motion capturing goniometer measuring variation in the angle of the joint through the position of the patch. More preferably, the motion capturing goniometer includes one or two cameras to two-dimensionally measure bent angle of the joint only.

In addition, the apparatus for lower-limb rehabilitation training may further comprise a signal processor for converting a value detected by the weight-measuring part and the joint angle-measuring part into an electric signal and transmitting the converted electric signal to the controller Preferably, the display part may comprise at least one selected from a group consisting of a monitor, an LED window and a dedicated monitor for a rehabilitation training machine in order to display the result data generated by the controller In order to realize the above objects, the invention provides a method for lower-limb rehabilitation training which uses weight load and joint angle, comprising steps of:

(a) at a load-measuring part, measuring weight loaded on a lower limb to generate weight data of the measurement data, and at a joint angle-measuring part, measuring the angle of a joint of the lower limb to generate joint angle data of the measurement data;

(b) generating weight data and joint angle data of reference data;

(c) comparing the weight data of the measurement data with the weight data of the reference data to generate weight comparison data and comparing the joint angle data of the measurement data with the joint angle data of the reference data to generate comparison data;

(d) generating condition data through the weight comparison data and the joint angle comparison data;

(e) generating result data including at least one of the condition data, the weight comparison data, the joint angle comparison data, the weight data of the measurement data, the joint angle data of the measurement data, the weight data of the reference data and the joint angle data of the reference data; and (f) displaying the result data to a user.

Preferably, the measurement data may include time data of the measurement data generated by counting a time period until the weight data of the measurement data becomes substantially the same afterward, and the method may further comprise a step of: generating time data by counting a time period until the weight data of the reference data becomes the same afterward and including the time data as of the reference data. Preferably, the method for lower-limb rehabilitation training may further comprise: receiving basic information of the user before the step (b). More preferably, the basic information of the user may be used for generating reference data including at least one selected from a group consisting of weight data, joint angle data and time data.

Preferably, the rehabilitation training allows the user to load weight as much as possible on one lower limb and bend the weight-loaded lower limb thereby training muscles of the weight-loaded lower limb to have power for burdening the weight. Alternatively, the rehabilitation training may be a balance training in which the user trains muscles by repeating actions of touching the floor with toes of both lower limbs while alternatively raising heels in order to evenly load weight on the both lower limbs; a standing training in which the user trains muscles necessary for both lower limbs to bend or straighten knees of the both lower limbs by touching the floor with the soles of the both lower limbs and at the same time bending and straightening the knees; or a walking training in which the user trains muscles necessary for normal walking by repeatedly performing an action of alternatively raising and lowering lower limbs with the foot sole thereof not touching the floor so that the powers for raising legs and for bending knees are analyzed.

Preferably, the rehabilitation training may irregularly represent at least one action selected from a group consisting of loading maximum weight on one lower limb and bending the knee of the weight-loaded lower limb, standing, balance training and walking so that the user perform the action as represented.

Preferably, the result data of the rehabilitation training may be generated by selecting either one of the reference data and the measurement data each including at least one of weight data, joint angle comparison data and time data, and comparing the value of the selected data, which is taken half-period before the present time, with the present value of the unselected data, so that comparison value is generated with respect to equal lower limb condition.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENT

The detailed description will present preferred embodiments of the invention with reference to the accompanying drawings.

Figure 1:
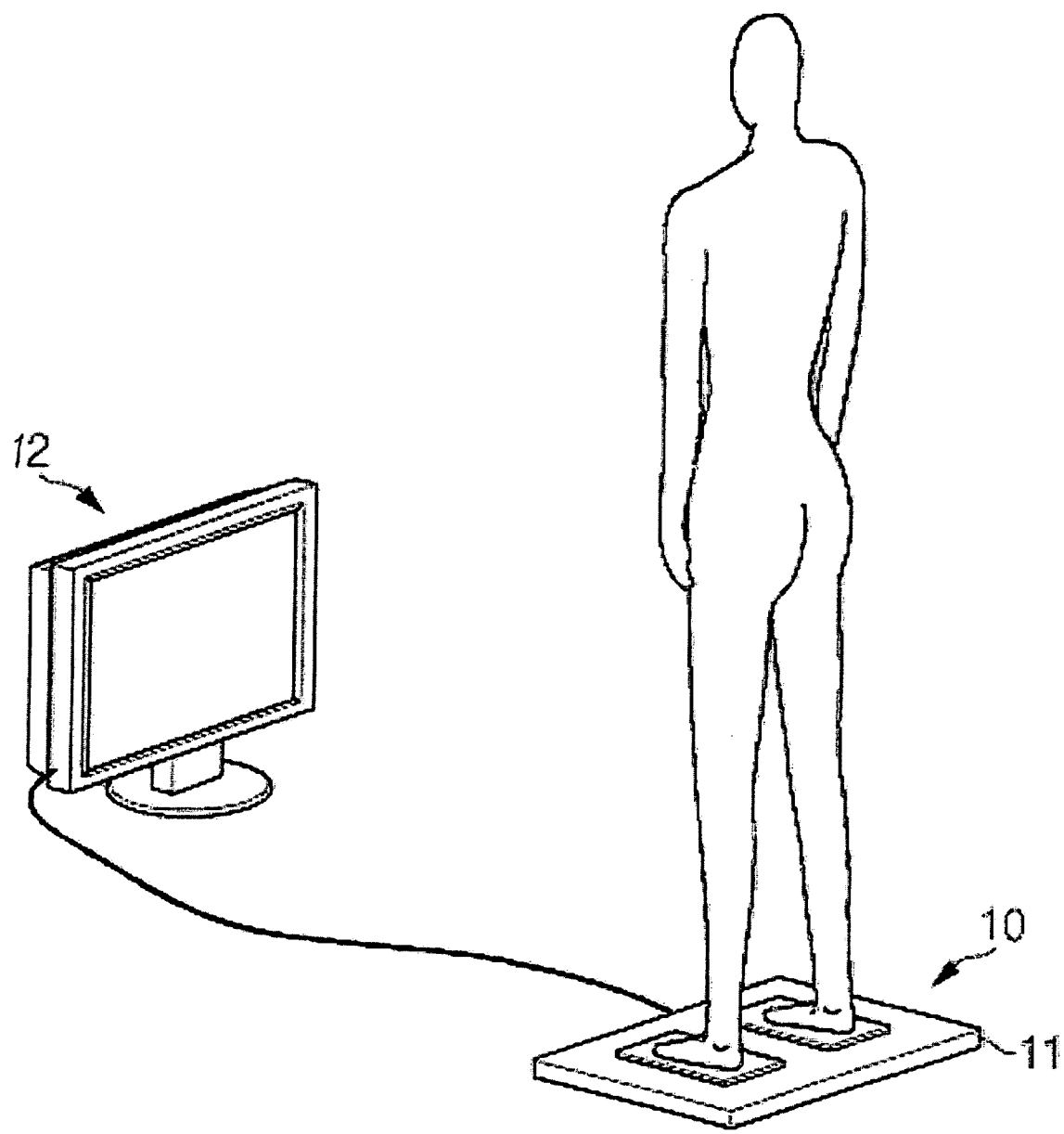
FIG. 1 illustrates a conventional apparatus for rehabilitation training using weight load and its user.
Figure 2:
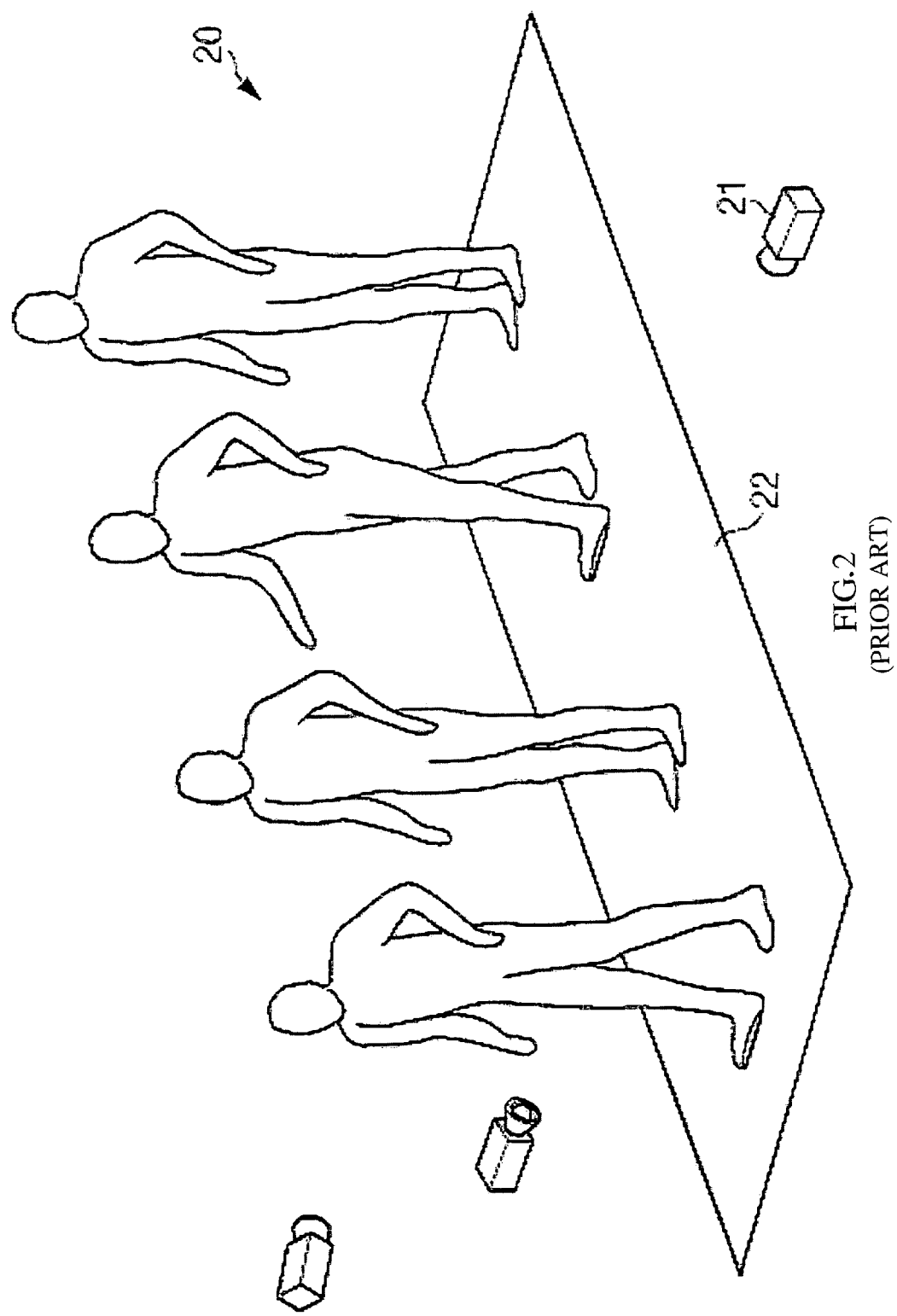
FIG. 2 illustrates a conventional three-dimensional walking analysis system using three cameras and a force plate.
Figure 3:
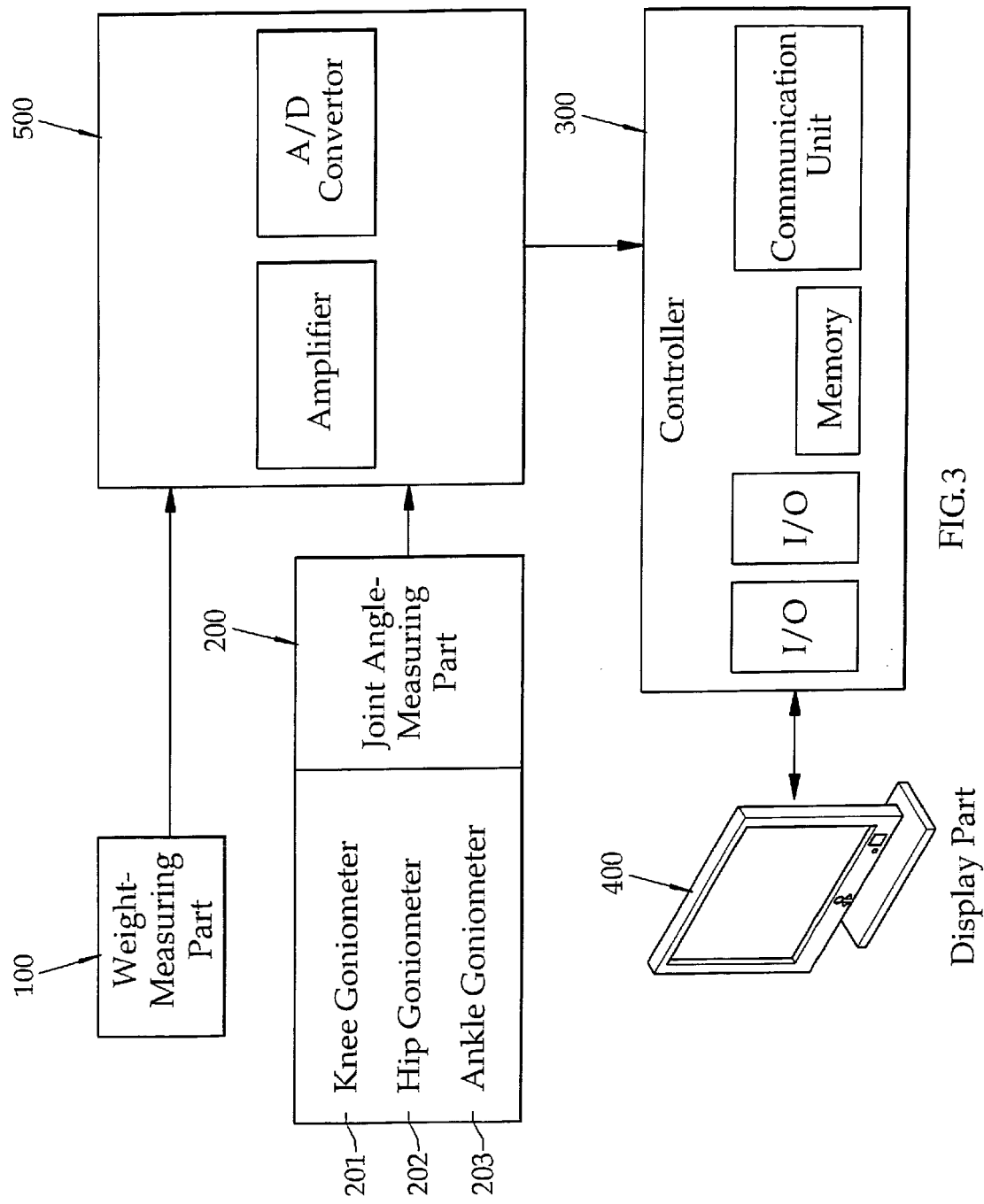
FIG. 3 is a block diagram illustrating an apparatus for lower-limb rehabilitation training of the invention.

FIG. 3 is a block diagram illustrating an apparatus for lower-limb rehabilitation training using weight load and joint angle according to the invention. As shown in FIG. 3, the apparatus for lower-limb rehabilitation training includes a weight-measuring part 100, a joint angle-measuring part 200, a controller 300 and a display part 400.

The weight-measuring part 100 is a part for measuring weight load that varies according to user motion, and disposed at a position contacting the bottom of a lower limb in order to measure the weight loaded on a lower limb. The weight-measuring part 100 may be provided to measure only one lower limb, which may be a paralyzed one. Of course, the weight-measuring part 100 can be configured to measure the weight loaded on both lower limbs.

Figure 4A:
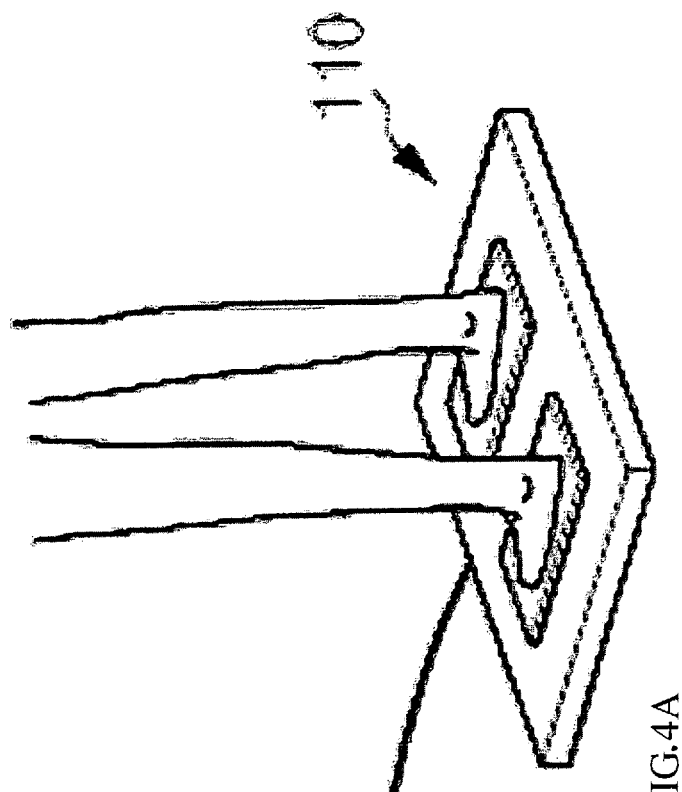
FIGS. 4a and 4b illustrate a force plate and a balance as a weight-measuring part.
Figure 4A:
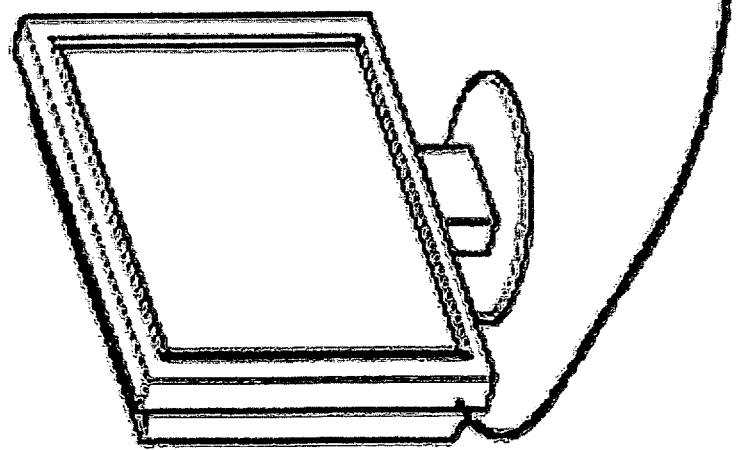

As shown in FIG. 4a, a force plate 110 including at least one pressure sensor that contacts directly or indirectly the bottom of the lower limbs may be used as the weight-measuring part 100. The pressure sensor can change its own status in response to the pressure, such that the weight loaded on the lower limbs can be measured based upon the changed status of the pressure sensor. In addition, at least one sensor may be attached to the bottom of each lower limb in order to measure the weight loaded to the lower region of the each lower limb.

Figure 4B:
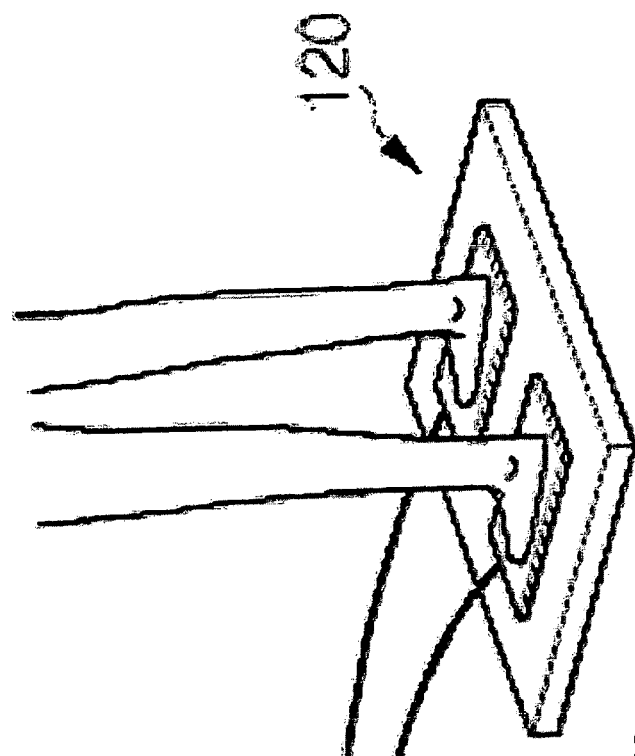
Figure 4B:
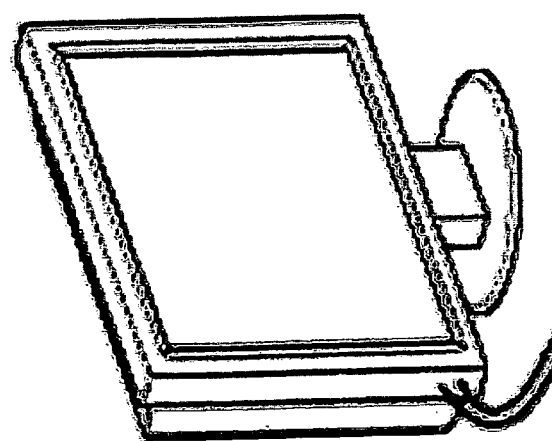

As shown in FIG. 4b, a balance 120 including an elastic mechanism that directly or indirectly contacts a lower region of the lower limb can be adopted as the weight-measuring part 100. The elastic mechanism of the balance 120 can vary its status under the weight loaded onto the lower limb in order to measure the weight loaded onto the lower limb. The varying status of the elastic mechanism may include but not limited to the volume or length.

The joint angle-measuring part 200 comprises at least one of a knee joint goniometer 201 for measuring the angle of a knee joint, a hip joint goniometer 202 for measuring the angle of a hip angle and an ankle joint goniometer 203 for measuring the angle of an ankle joint.

The joint angle-measuring part 200 may use an electric goniometer 210, a variable resistance goniometer 220 and a motion capture goniometer 230 in order to measure the angle of joints (e.g., knee joint, ankle joint and hip joint).

Figure 5:
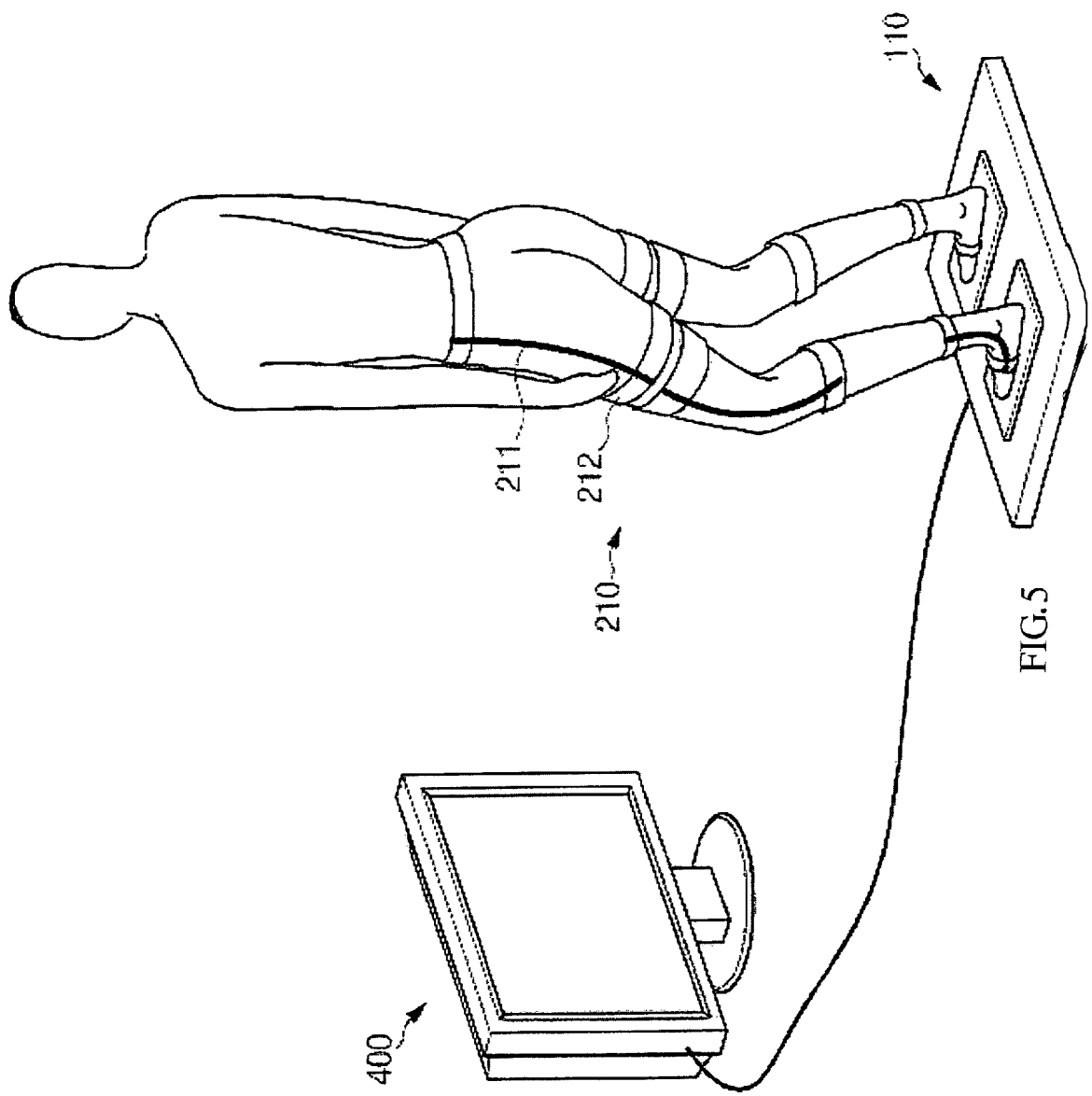
FIG. 5 illustrates an electric goniometer as a joint angle-measuring part.

FIG. 5 shows the electric goniometer 210 usable for the joint angle-measuring part 200. As shown in FIG. 5, the electric goniometer 210 includes a flexible bar 211 made of an elastic material so as to flex along with the bending of the joint and an attachment support 212 connected to a region of the lower limb and the flexible bar 211 for allowing the flexible bar 211 to flex along with the joint. The attachment support 212 of the electric goniometer 210 is attached to upper and lower regions of the joint the angle of which is to be measured, and connected to the flexible bar 211 which is oriented in the same direction of the joint.

In the knee joint goniometer 201, the attachment support 212 is disposed along the thigh and the calf. The flexible bar 211 is connected to the attachment support 212, and oriented in the same direction along which the knee is to bend. In this way, the angle of the knee joint is measured based upon the degree of bending of the flexible bar 211 that flexes along with the knee joint. In the ankle joint goniometer 203, the attachment support 212 is disposed on the calf and the foot so that the flexible bar 211 connected to the attachment support 212 flexes along with changes in the angle of the ankle. In this way, the angle of the ankle is measured based upon the bending of the flexible bar 211. Also in the hip joint goniometer 202, the attachment support 212 is attached to the waist and the thigh and the flexible bar 211, which is oriented to the same direction of the hip joint changing its angle in response to the leg being raised, is connected to the attachment support 212 in such a fashion that the angle of the hip joint is measured based upon the degree of bending of the flexible bar 211.

Figure 6:
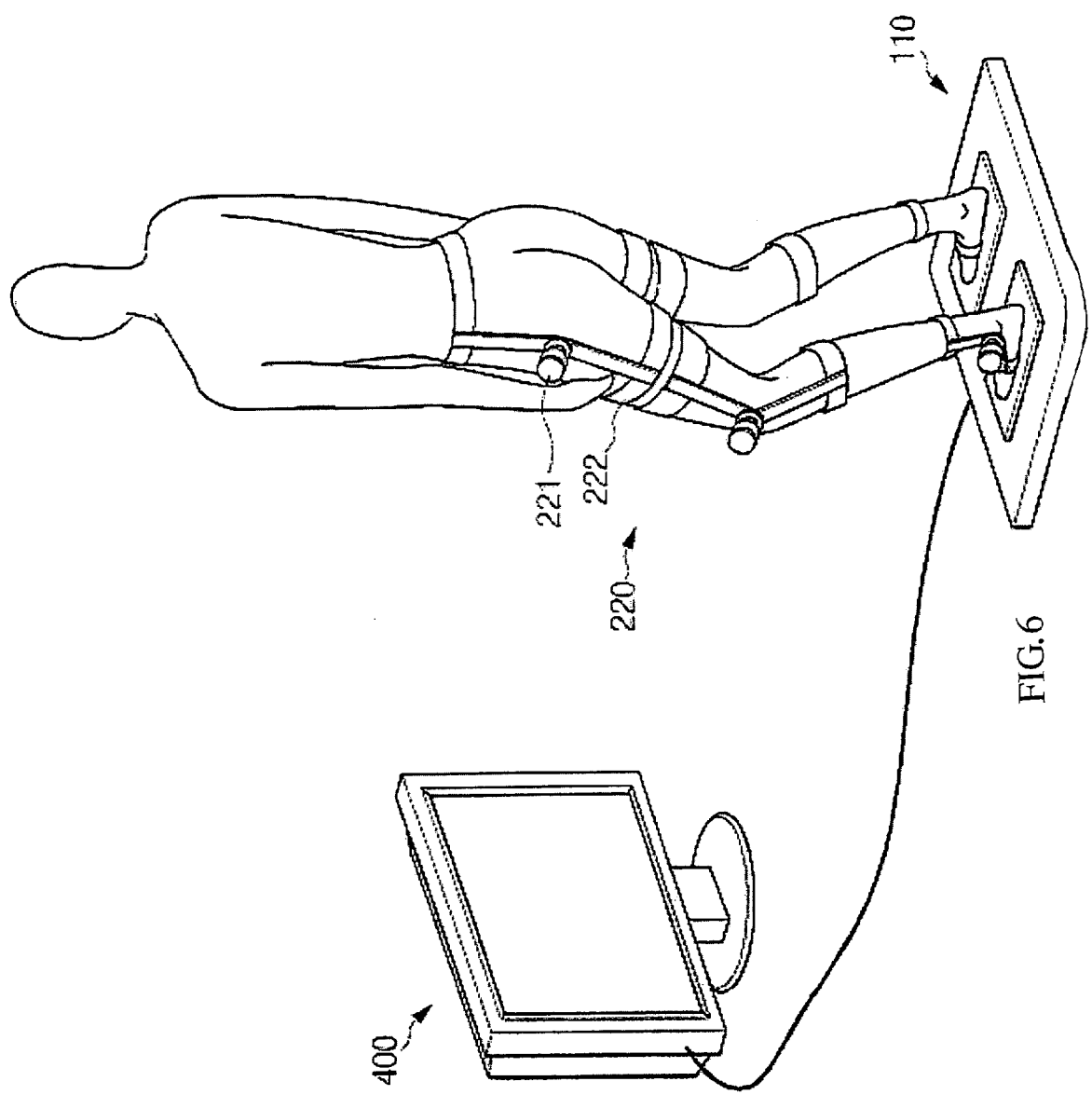
FIG. 6 illustrates a variable resistance goniometer as a joint angle-measuring part.

FIG. 6 illustrates the variable resistance goniometer 220 used as the joint angle-measuring part 200. As shown in FIG. 6, the variable resistance goniometer 220 includes a variable resistor 221, which is variable in resistance according to the angle of the joint, and an attachment support 222 for fixing the variable resistor 221 to the lower limb. Like the attachment support 212 of the electric goniometer 210, the attachment support 222 is placed on the thigh and the calf in case of the knee joint goniometer 201, on the thigh and the foot in case of the ankle joint goniometer 203, and on the waist and the thigh in case of the hip joint goniometer 202. The variable resistor 221 of the variable resistance goniometer 220 has a resistance adjustor that is provided to move along with the joint so that the resistance of the variable resistor is varied according to changes in the angle of the joint. In this way, it is possible to measure the angle of the joint based upon the resistance varying in response to the angle of the joint.

Figure 7:
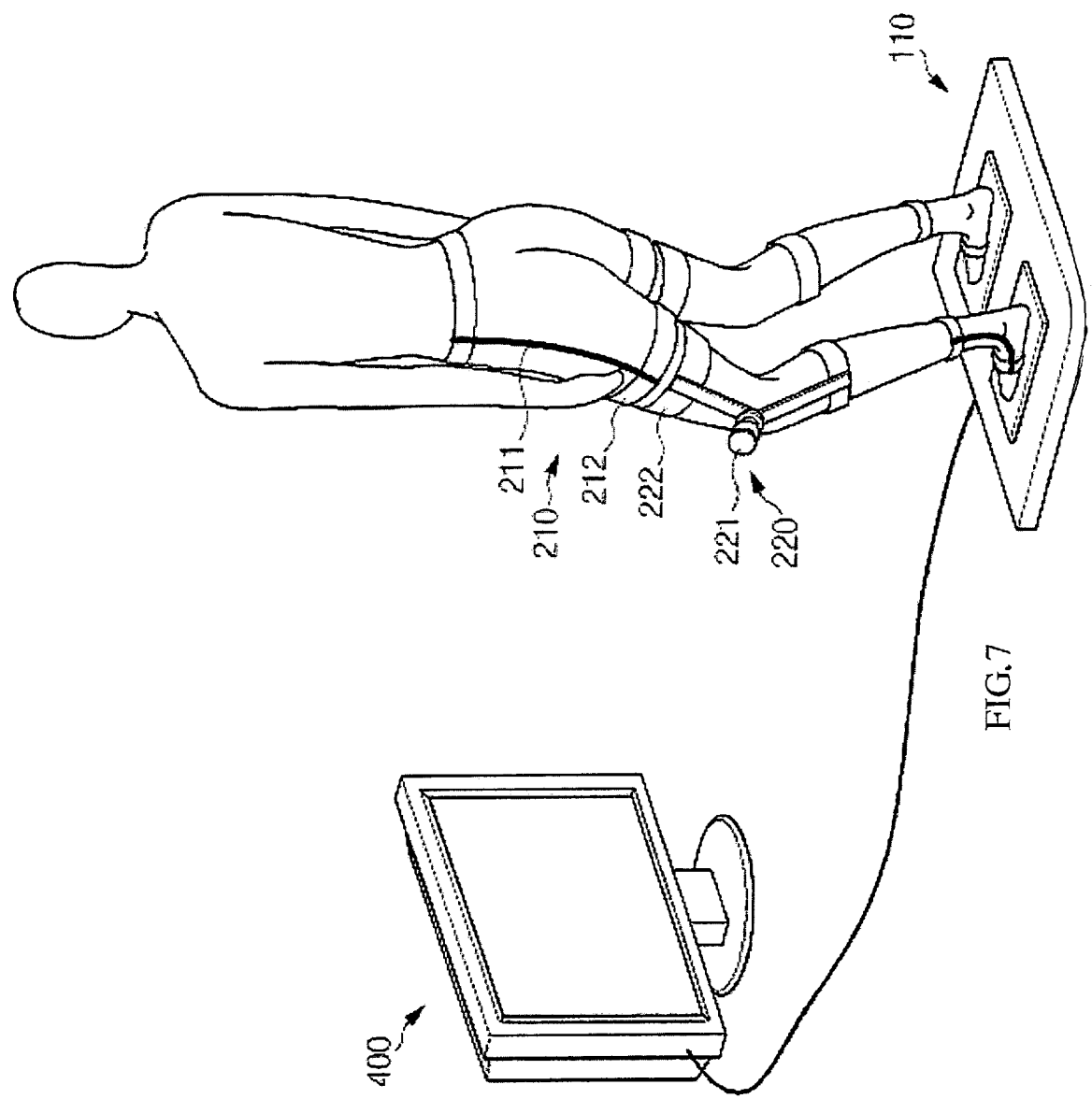
FIG. 7 illustrates electric goniometers used at the ankle joint and the hip joint and a variable resistance goniometer used at the knee joint.

Furthermore, as shown in FIG. 7, the joint angle goniometer 200 may adopt different goniometer types according to the knee, ankle and hip joints. For example, the knee joint goniometer 201 may adopt the variable resistance goniometer 220, and the ankle and hip joint goniometers 203 and 202 may adopt the electric goniometer 210. However, these are illustrative only, but the joint goniometer 220 may adopt any combination of goniometers.

Figure 8:
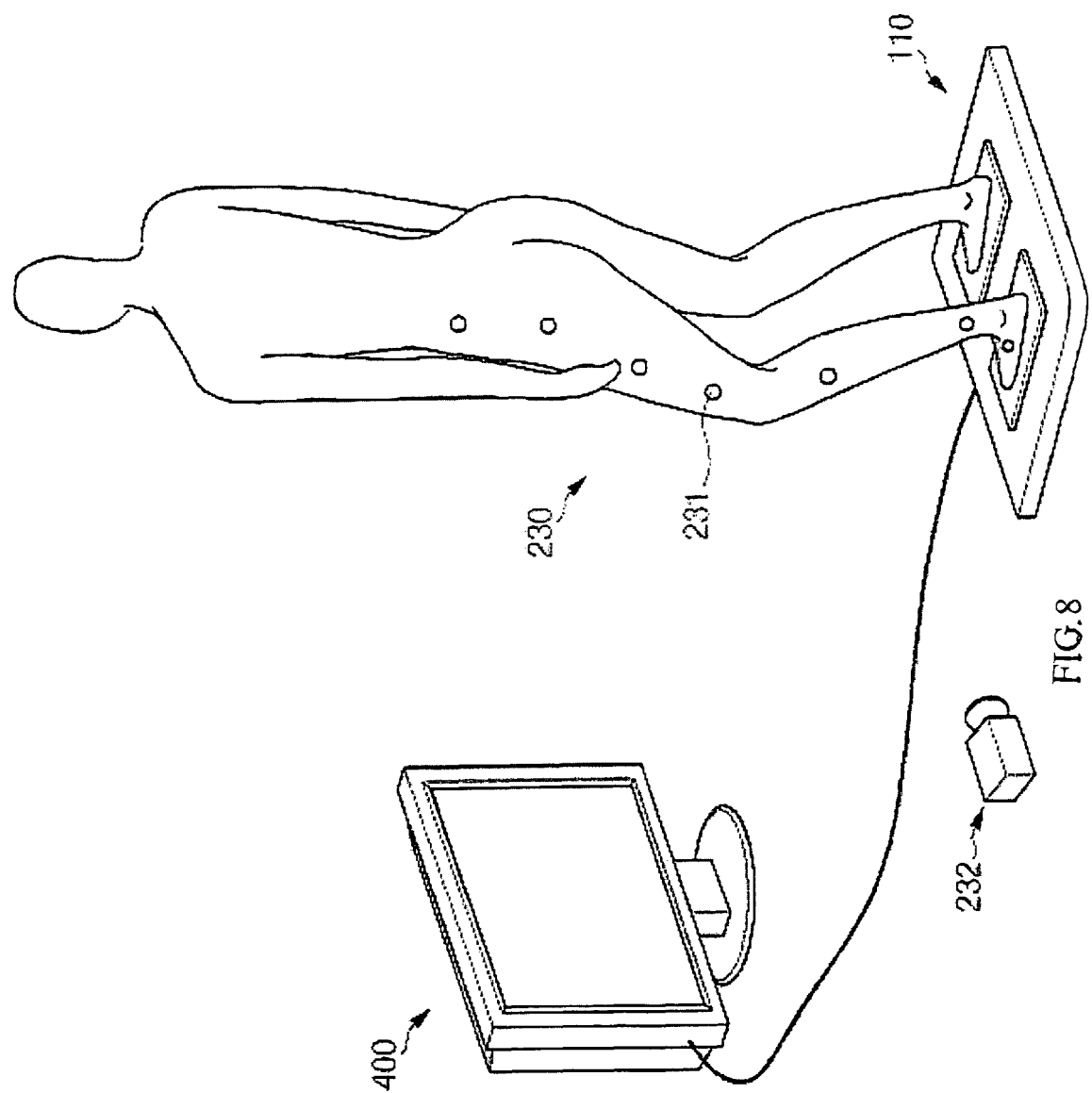
FIG. 8 illustrates a motion-capturing goniometer used as a joint angle-measuring part.

FIG. 8 illustrates the motion capture goniometer 230 used as the joint angle-measuring part 200. The motion capture goniometer 230 includes patches 231, which are attachable to the joint of the lower limb and limb regions above and under the joint, and a camera 232 that can detect the position of the patches 231. Then, the joint angle-measuring part 200 can detect the position of the patches 231 attached to the lower limb, varying in response to the movement of the lower limb by using the camera 232, and thus measure the angle of the joint through the varying position of the patches 231. The position of the patches 231 may be varied according to the knee, ankle and hip joint goniometers. For example, in the knee joint goniometer 201, the patches 231 are attached to the thigh and the calf, which are regions above and under the knee ankle. In the hip joint goniometer 202, the patches 231 are attached to the hip joint, the waist and the thigh. Furthermore, the patches 231 are preferably attached to those regions facing the camera 232 so that they can observe the patches 231. More preferably, the patches 231 are attached to side regions of the lower limb so that the camera 231 can measure the angle varying in response to the movement of the joint when the lower limb is raised or the knee is bent.

In addition, the apparatus for lower-limb rehabilitation training of the invention may also include an amplifier-converter 500 for converting data, which is measured in real-time by the weight-measuring part 100 and the joint angle-measuring part 200, into an electric signal. While the amplifier-converter 500 may be included in the weight-measuring part 100 and the joint angle-measuring part 200, it can be provided in the controller 300 or as a separate part.

Figure 9:
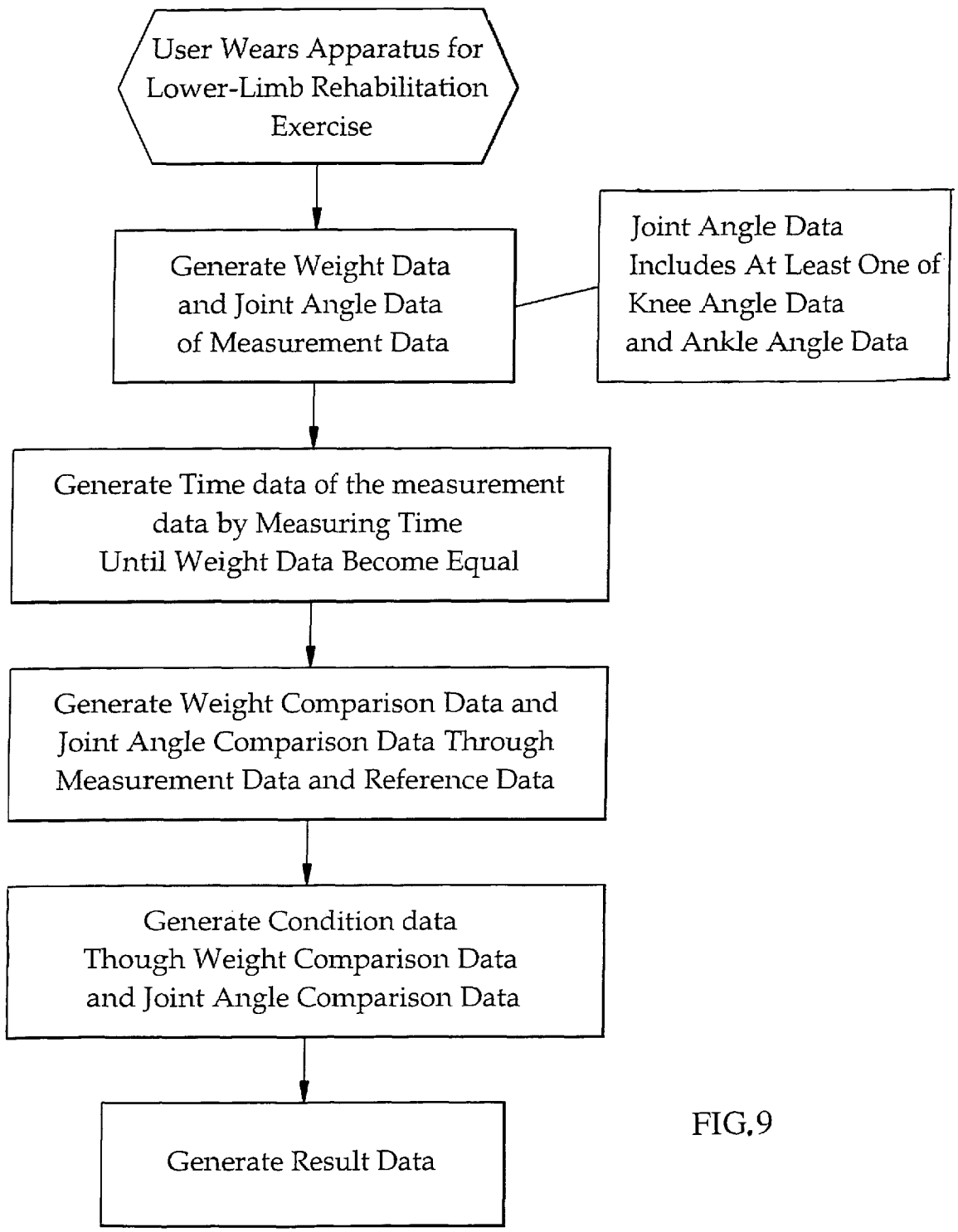
FIG. 9 is a flowchart illustrating a process executed by a controller.

In the apparatus for lower-limb rehabilitation training of the invention, based upon measurement data obtained from the weight-measuring part 100 and the joint angle-measuring part 200, the controller 300 generates result data to be displayed by the display part 400. FIG. 9 is a flowchart illustrating a process by the controller 300 for generating result data.

The controller 300 reads measurement values simultaneously from the weight-measuring part 100 and the joint angle-measuring part 200 or controls the weight-measuring part 100 and the joint angle-measuring part 200 to simultaneously implement measurement. The controller 300 also generates the value read from the weight-measuring part 100 into weight data of measurement data, and the value read from the joint angle-measuring part 200 into measured joint angle data. Since the joint angle-measuring part 200 includes at least one of the knee joint goniometer, the ankle joint goniometer 203 and the hip joint goniometer, the controller 300 accordingly generates the measurement data as knee angle data, ankle angle data and hip angle data.

In addition, the controller 300 counts time until the weight data of the measurement data becomes substantially the same value, and generates the counted time as time data of measurement data. The time data of the measurement data is generated since the time required for the paralyzed lower limb to move may be different from the time required for the normal lower limb to move. For example, since it is more difficult to move the paralyzed lower limb and walking requires more effort, the paralyzed lower limb may move in a shorter pace or take more time per step in walking. For this reason, the apparatus for lower-limb rehabilitation training of the invention measures the time elapsed during the movement of the paralyzed lower limb to generate measurement time data so that the measurement time data can be compared with reference time data required for a normal lower limb to move. Then, the controller generates time comparison data from the difference between the measurement time data and the reference time data.

The reference data functions as a reference with which the measurement data is to be compared, and includes at least one of weight data, knee angle data, ankle angle data, hip angle data and time data like the measurement data including at least one of weight data, knee angle data, ankle angle data, hip angle data and time data. The reference data may be generated through the measurement of the lower limb of normal people similar to previously stored basic information of the user, or through estimation. Otherwise, the reference data may be measured in real-time from the normal lower limb of the patient having the paralyzed lower limb, from which the measurement data are generated. If the measurement data is taken in real-time from the normal lower limb, in order to compare the conditions of the both lower limbs in the same position, it is preferable that one is selected from the measurement data and the reference data, and the value of the selected data, which is taken half-period before the present time, is compared with the present value of the unselected data.

The controller 300 compares the weight and joint angle data of the measurement data with the weight and joint angle data of the reference data to generate weight and joint angle comparison data. The joint angle data includes at least one of the knee angle data, the ankle angle data and the hip angle data as described above, and accordingly the joint angle comparison data includes at least one knee angle comparison data, ankle angle comparison data and hip angle comparison data.

In addition, when the measurement data is compared with the reference data in order to generate the weight comparison data and the joint angle comparison data, it is enough to confirm whether or not the measurement data and the reference data are similar. So, subtraction and/or division can be selectively used. Subtraction generates comparison data from the difference, and division generates comparison data from the ratio. It is apparent that the invention can use at least one of the above-described methods in order to generate the comparison data.

Then, through the weight comparison data and the joint angle comparison data, the controller 300 generates condition data numerically informing the usage of paralysis. The condition data can be produced from the weight comparison data with the joint angle comparison data by addition or multiplication. These operations for producing the condition data are illustrative only, but other operations may be adopted to produce the condition data.

If the condition data is within an error range, the controller 300 generates a message informing that the usage of lower limb muscle or its rehabilitation training is normal. The condition error can be set according to the user, or used as values previously stored in the apparatus. The condition error can be varied according to operations for generating the condition data.

Based upon the condition data, the weight comparison data and the joint angle comparison data, it is possible to generate a message available for feedback training of the user.

If the condition data is out of the error range, in order to judge which part of the paralyzed lower limb disables the lower limb from normally moving, first the weight comparison data is detected, and if the weight comparison data is within the error range, the joint angle comparison data is detected. This order of detection may be set different according to the user, training purpose or training method. That is, the weight comparison data can be detected after the detection of the joint angle comparison data. In case of balance or standing training, the weight comparison data will be dominant in the condition data since a patient with lower-limb paralysis is unlikely to strain the paralyzed lower limb. However, in case of walking training where the total weight is repeatedly concentrated on one lower limb and then on the other lower limb, the condition data is influenced unlikely by the weight data but likely by the joint angle comparison data. It is highly probable that the condition data can be out of the error range by the joint angle comparison data. Thus, it is preferable that the joint angle comparison data is first detected for the purpose of rapid process.

If the weight comparison data is out of the error range, there is generated a message instructing that the weight load be further biased to the lower limb under the measurement or reduced according to the importance of the reference data and the measurement data.

The joint angle comparison data will be detected as follows. In detection of the joint angle comparison data, if all of the knee, ankle and hip angles are measure, the knee angle comparison data is detected first, and if the knee angle comparison data is within the error range, a message is generated with respect to a bigger one of the ankle angle comparison data and the hip angle comparison data. If the knee angle comparison data is out of the error range, the controller 300 generates a message instructing that the knee be further bent or straightened according to the importance of the measurement data and the reference data.

If the knee angle comparison data is within the error range of the knee angle, a larger one is selected from the ankle and hip angle comparison data as described above. If the ankle angle comparison data is larger than the hip angle comparison data, there is generated a message instructing movement of the ankle with further or less bending thereof according to the importance of the ankle angle data of the reference data and the ankle angle data of the measurement data. If the knee angle comparison data is smaller than the hip angle comparison data, there is generated a message instructing movement of the leg with further raising or less raising thereof according to the importance of the hip angle data of the reference data and the hip angle data of the measurement data.

Then, the controller 300 generates a result data to be transmitted to the display part. The result data includes at least one selected from the group consisting of time data, weight data, knee angle data, ankle angle data and hip angle data of the measurement data; time data, weight data, knee angle data, ankle angle data and hip angle data of the reference data; weight comparison data, knee angle comparison data, ankle angle comparison data, hip angle comparison data, time comparison data and condition data. The result data may also include a message that is so generated for allowing the user to suitably training.

Figure 14:
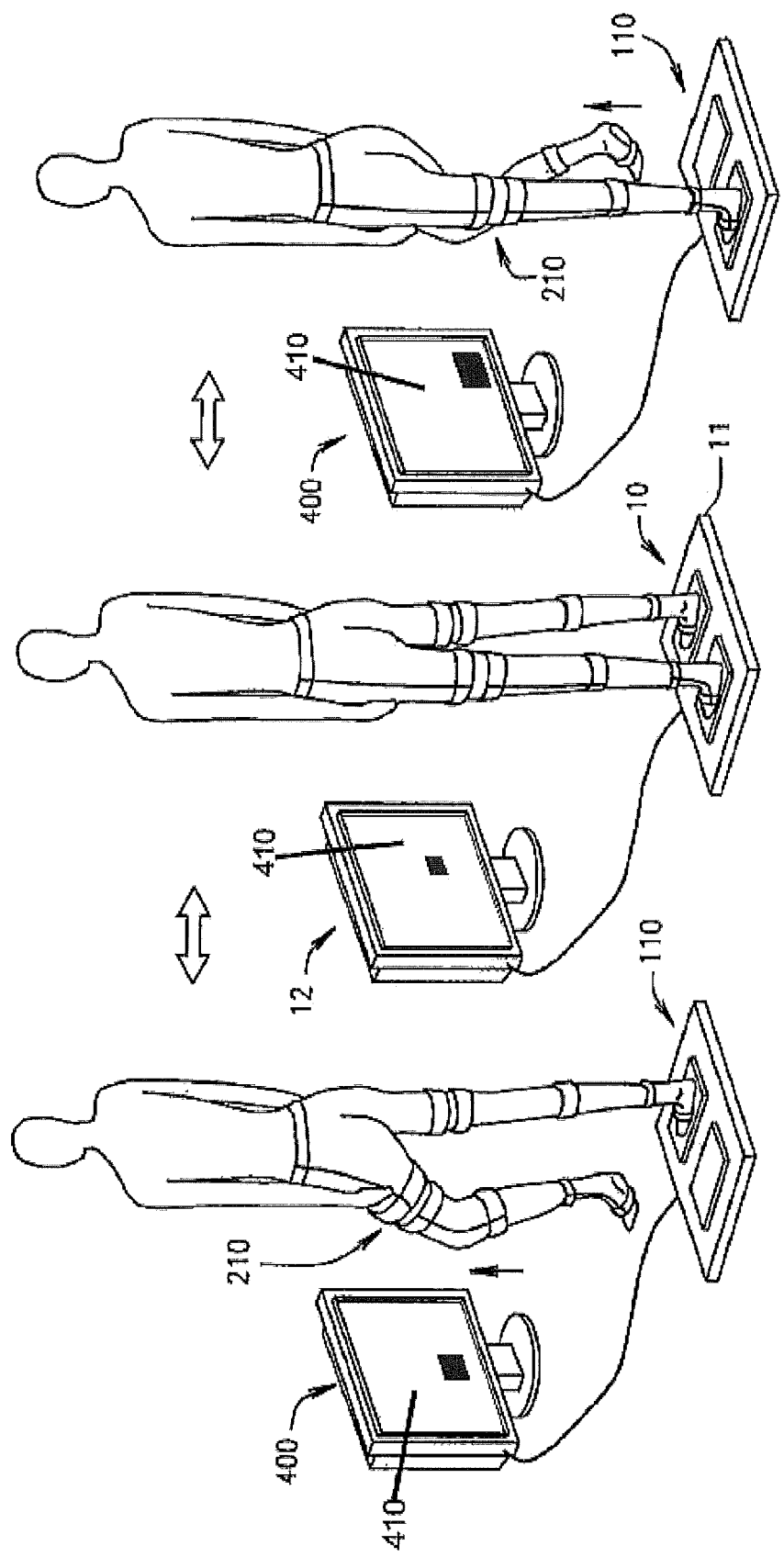
FIG. 14 illustrates an exemplary view of playing a computer game controlled by a force plate and goniometer associated with a user, constructed in accordance with the teachings of the present invention.

In addition, the controller may generate a game using the result data as variables so that the user can enjoy training. Examples of the game may include TETRIS® game 410 as shown in FIG. 14, castling and so on.

A game similar to TETRIS® (hereinafter will be referred to as "bricking") provides a groove in a lower part of a screen on which the game 410 is displayed. Of course, the groove may be located in the right, left or middle. The size of the groove may be varied.

As a brick drops from above, the user examines the location of the groove formed in the lower part of the screen, and the moves his/her weight to the right or left according to the location of the groove in order to move the brick to the right or left. That is, if the groove is located in the right, the user is supposed to load the weight to the right, and the groove is located in the left, the user is supposed to load the weight to the left. The size of the brick is varied according to the angle of the joint. If the joint angle is small, the brick size may be kept small. If the knee is bent at a larger angle, the brick size will grow. When the brick has correct size and location matching the groove and thus enters to the groove, the task is deemed successful. After that, a new task is presented with a screen displaying a groove in a different location. Through the "bricking", the patient can take training to adjust the movement of the joint while loading the weight on the paralyzed leg.

In addition, a game similar to the castling (hereinafter will be referred to as "castling") increases the size of stones as more weight is loaded on the paralyzed lower limb, the joint angle is increased, or the time for maintaining such a posture is prolonged. For example, the stone size is adjusted by varying the width of the stone by the weight, the length of the stone by the joint angle, and the height of the stone by duration time. If the weight is moved by a large quantity, the knee is bent by a large angle, and this posture is maintained by a long time, the castling is carried out with large stones. If the weight is moved by a small quantity, the knee is bent by a small angle, and this posture is maintained by a short time, the castling is carried out by small stones. The total volume of the stones may be directly counted as scores or graded as a part of the game. The castling is a game to induce the user to move the weight and bend the joint as much as possible.

As illustrated with the TETRIS® and the bricking or castling, the user can be more interested in training by playing a game using the result data as variables of the game.

Figure 10:
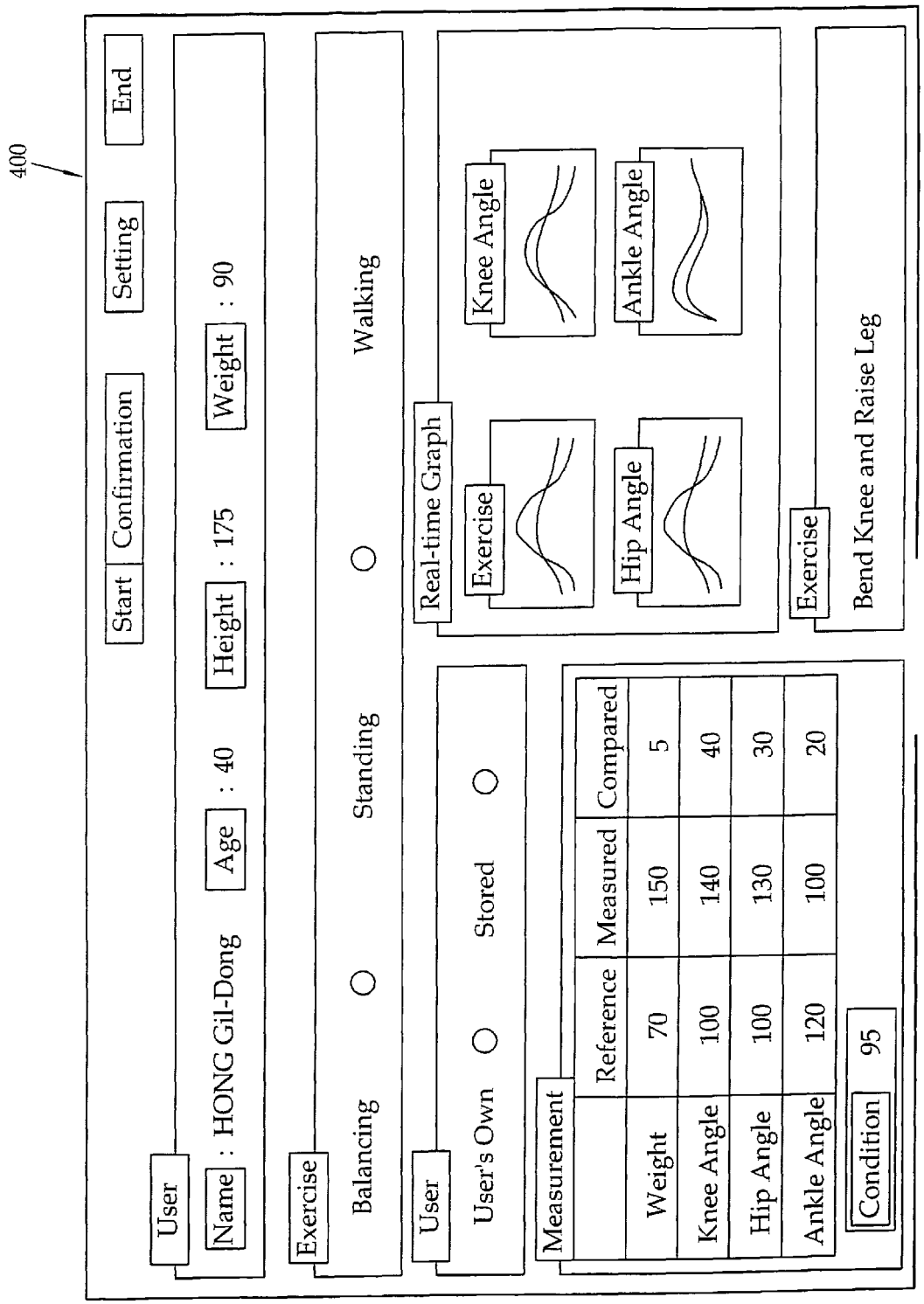
FIG. 10 is a diagram illustrating a screen of a display part.

The apparatus for lower-limb rehabilitation training of the invention includes the display part 400 for displaying result data generated from the controller 300 to the user. As shown in FIG. 10, examples of the display part 400 may include a dedicated monitor, a display board, an LED window, a general computer monitor and so on that can be used to display contents to the user in the apparatus for lower-limb rehabilitation training.

The display part 400 displays basic information including name, age, weight and height of the user and result data generated by the controller. Furthermore, the display part 400 can use characters or sign lamps to display messages associated with user condition of the result data generated by the controller 300 so that the user can easily notice. This is an example only, but the invention is not limited thereby.

In displaying the result data generated by the controller 300, the display part 400 can plot a graph with time on one axis and data on the other in order to assist the user to recognize the usage of the paralyzed muscle.

In case of the weight data graph, the weight data of the reference data and the weight data of the measurement data measured in real-time are displayed on the graph with time on one axis and the weight data on the other axis. The user can easily recognize whether or not two data are similar, and can training the paralyzed lower limb in order to make the two data similar.

In case of a knee angle data graph, the knee angle data of the reference data and the knee angle data of the measurement data, measured in real time, are displayed on the graph with time on one axis and the knee angle data on the other axis. Hip and ankle angle data graphs are plotted similar to the above-described knee angle data graph.

Furthermore, the condition data may be displayed on a graph with the condition data, which are generated through the weight comparison data and the joint angle comparison data, on one axis and time on the other axis. The slope of the condition data graph will decrease as the user trainings properly.

Of course, different processes may be adopted to generate the graphs in condition that they comply with the purpose of allowing the user to easily notice his/her condition in real-time.

In addition, the result data can be expressed by numbers or characters other than the graphs. A data having the largest value of the condition data, the weight comparison data and the joint angle comparison data can be displayed via an LED so that the user can easily recognize a region that should be most trained in rehabilitation of paralysis.

The contents expressed by the numbers, characters and graphs may be varied whenever data are newly measured and added.

A reference will now be given to an embodiment of a method for lower-limb rehabilitation training using the apparatus for lower-limb rehabilitation training based upon weight load and joint angle.

The invention proposes lower limb rehabilitation training in which the user performs task actions once or repeatedly to recognize the usage of the paralyzed muscle via the apparatus for lower limb rehabilitation training. Furthermore, in order to improve the recognized condition of paralysis, the user repeatedly corrects the task actions or the task actions are continuously changed so that the user carries out the varying task actions.

Examples of the task actions may include bending the knee of one lower limb with the weight loaded on the lower limb by a maximum amount, simultaneously bending the knees of both lower limbs with feet soles touching the floor, raising the heels of both feet with their toes touching the floor and walking in the same place. These actions are examples of the method for lower limb rehabilitation training, but the task actions may include any actions that can improve the usage of the paralyzed muscle of the user. Furthermore, the task actions can be corrected based upon the usage of the paralyzed muscle of the user.

In case that the task action is to bend the knee of one lower limb with the weight loaded on the lower limb by a maximum amount, the user can enhance muscular power for loading more weight to the paralyzed leg as well as for more bending the knee of the paralyzed leg while performing the task action. As a result, it is possible to improve the problem of a patient with partial paralysis that the patient can hardly support the weight with the paralyzed lower limb while bending the knee thereof.

Furthermore, as described above, the lower limb rehabilitation training may adopt a method for varying task actions so that the user can train all muscles or motors necessary for training while performing the varying task actions. The varying task actions may be displayed in such a fashion that the user can perform actions along with a varying graph or by letters or a display unit such as LED. These are examples only, but any method for allowing the user to recognize the task actions as soon as possible can be apparently adopted without departing from the purpose of the invention.

The task actions illustrated as above will now be described in more detail.

Balance Training

Figure 11:
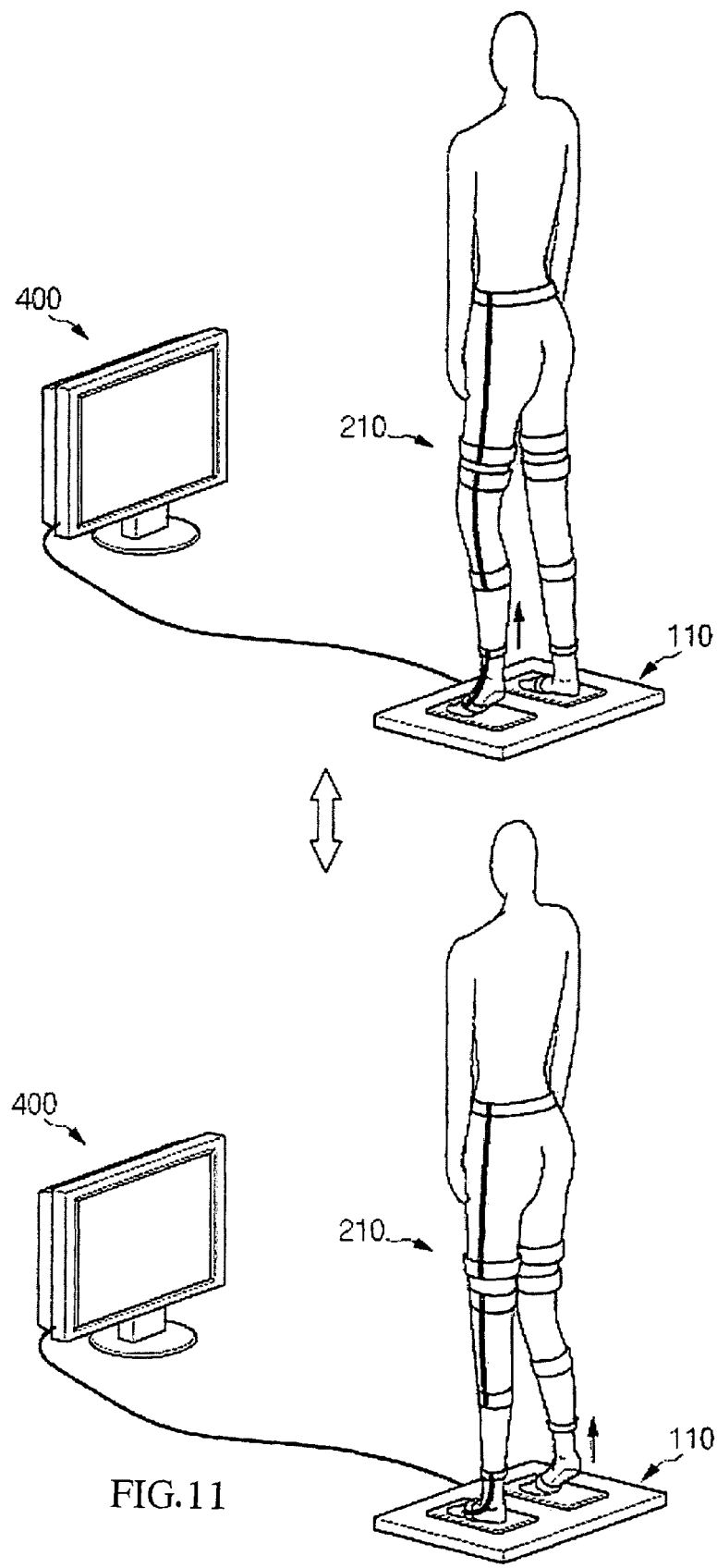
FIG. 11 illustrates a balance training of a user.

FIG. 11 illustrates a balance training of a user. The balance training can be performed in such a way that the user raises heels alternatively with toes of both lower limbs touching the floor in order to load weight on the paralyzed lower-limb.

Before performing the balance training, an apparatus for lower-limb rehabilitation training utilizing weight load and joint angle is attached to the user. In the apparatus for lower-limb rehabilitation training adapted to measure joint angle, the joint angle-measuring part 200 may include at least one of the knee joint goniometer, the ankle joint goniometer and the hip joint goniometer 202.

As shown in FIG. 11, the balance training repeats alternatively raising the heels with the toes touching the floor, in which one foot is lowered with total sole of the foot touching the floor or the weight-measuring part 100 while the heel of the other foot is raised with toes thereof touching the floor.

For example, it is assumed that the user performing the balance training is a patient with paralysis in right lower limb. The apparatus for lower-limb rehabilitation is attached to the patient with lower-limb paralysis, and then the patient starts training. It is also assumed that the joint angle-measuring part 200 of the apparatus for lower-limb rehabilitation includes all of the knee, ankle and hip joint goniometers. While the reference data necessary for the user may be generated previously by adopting a step of inputting the weight, height, age and so on of the user before the start of training, it is assumed in the following description that the normal left lower limb is measured at the same time to generate the data of the left lower limb as the reference data.

In case of setting the reference data by the data measured from the normal lower limb, the heels of the normal and paralyzed lower limbs are alternatively raised. So, in order to compare the conditions of the normal and paralyzed lower limbs with the heels raised, those data measured at the same time are not compared with each other. Instead, one is selected from the measurement data and the reference data, and the value of the selected data, which is taken half-period before the present time, is compared with the present value of the unselected data.

As the user raises the heel of the left lower limb, the angle of the ankle becomes larger while the angle of the knee becomes smaller. Since the leg is raised merely slightly, the angle of the hip becomes larger from about 180°. Also, the weight is biased to the right lower limb, and the center of the weight also moves toward the right lower limb. When the heel of the left lower limb is dropped with the whole part of the foot sole of the left lower limb touching the floor and the heel of the right lower limb is raised, the weight biased on the right lower limb moves to the left lower limb and the joint angle of the right tower limb changes. As assumed above, compared to the left lower limb, raising the heel of the paralyzed right lower limb will show differences in the degree of raising the lower limb, the degree of bending the knee and the degree of reducing the angle of the ankle. In addition, the time necessary for raising the heel of the paralyzed lower limb will be different from the time necessary for raising the heel of the normal lower limb. Therefore, following estimation can be made to the measurement data including weight data, joint angle data and time data; and the reference data including weight data, joint angle data and time data.

Provided that the paralyzed right lower limb has a smaller force for raising the leg than the left lower limb, the degree of biasing of the weight from the right leg to the left leg will be small. In addition, the paralysis of the right lower limb will make it difficult bend its knee as well as dorsiflex its ankle. Accordingly, it is assumed that the weight data of the measurement data (i.e., the measurement value on the right lower limb) will be larger than the weight data of the measurement data (i.e., the measurement value on the left lower limb) and any measurement data obtained by the comparison of the two weight data will be beyond an error range of weight. It is also assumed that the knee angle data of the measurement data will be smaller than the knee angle data of the reference data and any knee angle comparison data generated through the two knee angle data will be beyond an error range of knee angle. In addition, the ankle angle data of the measurement data will be smaller than the ankle angle data of the reference data and the hip angle data of the measurement data will be smaller than the hip angle data of the reference data. Provided that any condition data obtained through the respective comparison data are beyond a condition error range, there is generated a message instructing that the weight be further loaded on the left lower limb according to the importance of the weight data of the reference data and the weight data of the measurement data. The message is displayed on the display part 400, included in result data.

When the user refers to the message, if the condition data is beyond the error range but the weight data is within the error range, the user detects whether or not the knee angle comparison data is within the error range. Since it is assumed that the knee angle comparison data is beyond the error range and the knee angle data of the measurement data is smaller than the knee angle data of the reference data, the controller 300 of the apparatus for lower-limb rehabilitation training generates a message instructing that the knee of the right lower limb be further bent. The message is displayed on the display part 400, included in result data.

If the condition data is out of the error range but the weight and knee angle comparison data are within the error range, detection is made to the importance of the knee angle comparison data and the hip angle comparison data. Provided that the hip angle comparison data is larger than the hip angle comparison data owing to weak force of the user for raising the lower limb, there is generated a message instructing that the right lower limb be further raised according to the importance of the hip angle data of the measurement data and the angle data of the reference data. The message is then included in the result data.

Furthermore, the time spent for raising the heel of the right lower limb will be longer than the time spent for raising the heel of the left lower limb. In response to it, through the measured and reference time data, there is generated a message instructing that the right lower limb be more positively used.

Through the balance training as described above, the patient with lower-limb paralysis can have training to use paralyzed muscle by loading the weight to the paralyzed lower limb.

Standing

Figure 12:
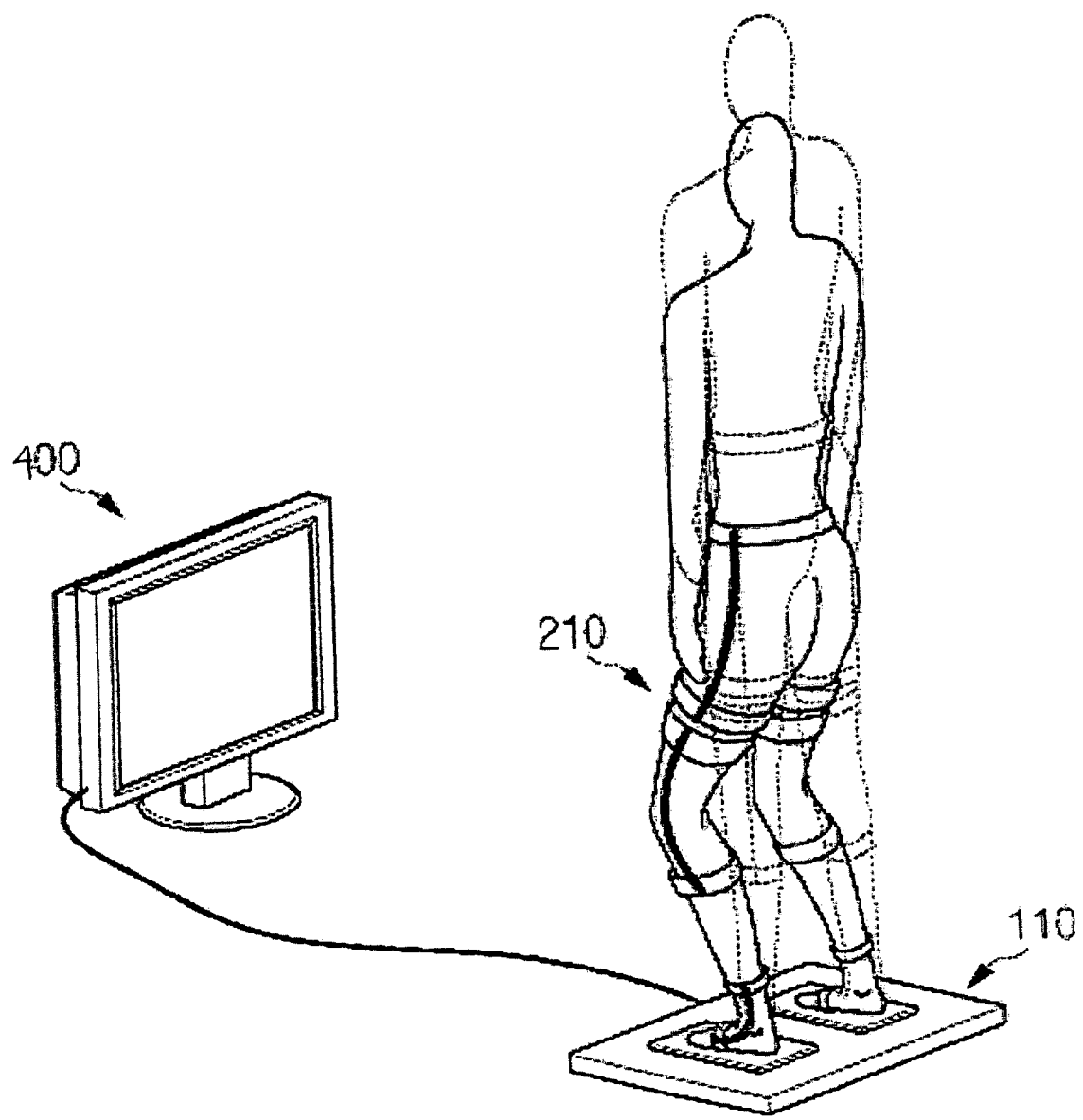
FIG. 12 illustrates a standing training of a user.

FIG. 12 illustrates a standing training of a user. In the standing training, the user with the apparatus for lower-limb rehabilitation training utilizing weight load and joint angle attached thereto repeats bending and straightening both knees. While bending and straightening both knees, the user trainings to bend the both knees simultaneously to the same angle within the same time period.

The above-mentioned balance training can utilize normal person's data previously stored in the apparatus for lower-limb rehabilitation training or data measured from a normal lower limb as the reference data to be compared with the measurement data of the paralyzed lower limb. In case of utilizing the data measured from a normal lower limb, the lower limb has the same weight load and joint angle. Unlike the balance training, the standing training utilizes simultaneously measured data in the comparison of the reference data with the measurement data.

Where a patient having paralyzed right lower limb takes a balance training, the apparatus for lower-limb rehabilitation is attached to the user so that the user starts the training. Before starting the training, basic information of the user can be inputted. While the basic user information is used for the identification of the user, it may also be used as data for setting the reference data in case of using the previously stored normal person's data. Through the standing training using the apparatus for lower-limb rehabilitation training proposed by the invention, the user can confirm whether or not the same weight load acts on both lower limbs. The user can also confirm whether or not the knee, ankle or hip angle is identical in the both limbs. As a result, in case of an abnormal standing posture where the user bends knees slightly while loading the weight similarly to both of the lower limbs, the training can help the user have a normal standing posture. That is, the user can bend the knees normally.

Walking

Figure 13:
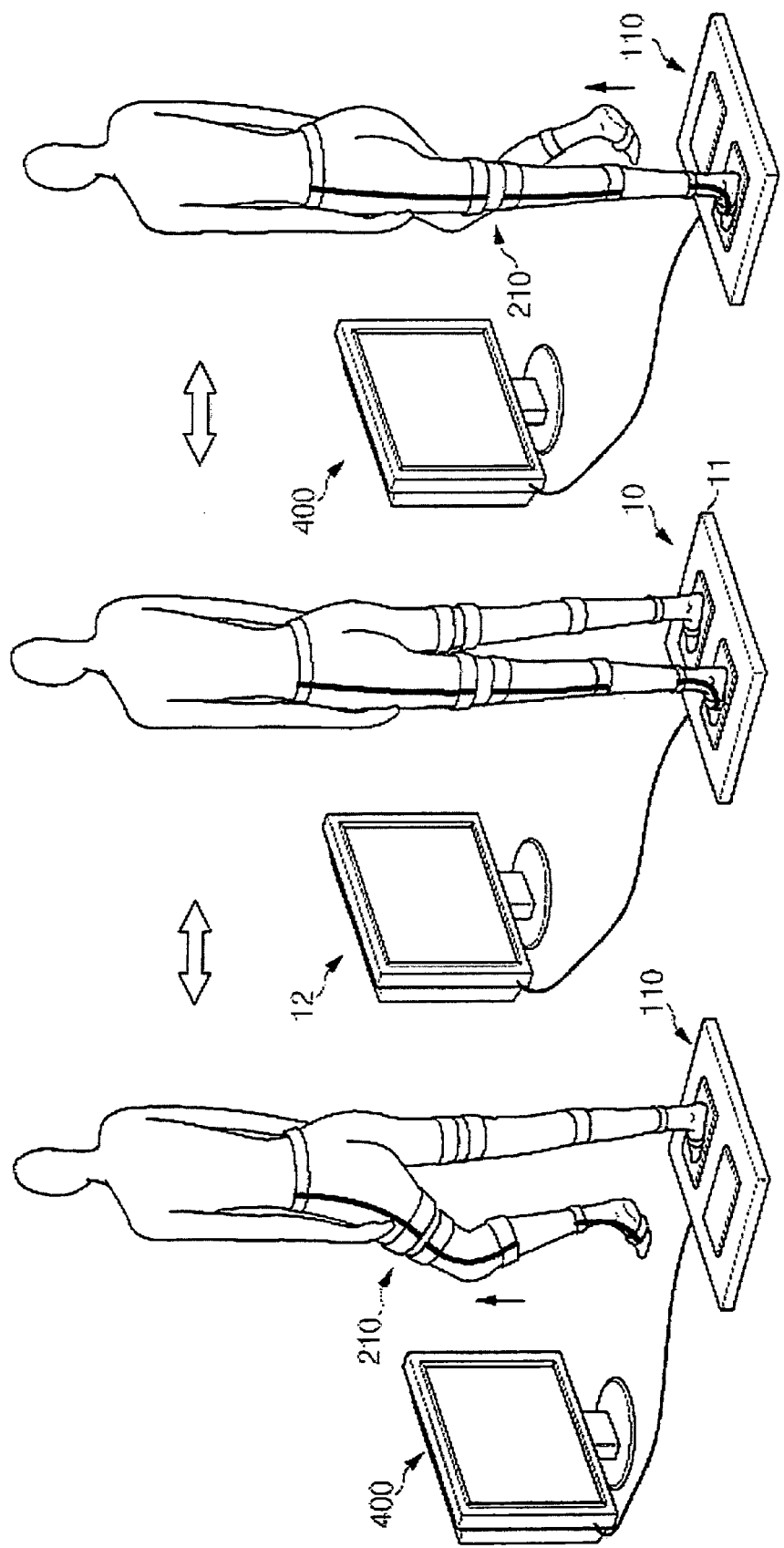
FIG. 13 illustrates a walking training of a user.

FIG. 13 illustrates a walking training of a user in a stepwise fashion.

A normal walking is carried out by organic movement of the joints of the lower limbs together with the weight load. Describing this in more detail, the walking training of this invention means that the user repeats walking in the same place. As a normal walking in the same place, when the total weight is loaded on the first lower limb, the user raises the second lower limb with its knee bent. Then, the user lowers the raised lower limb down, and at the same time, raises the first lower limb with the foot sole touching the floor and bends the knee of the first lower limb. These actions are repeatedly performed.

In the walking training, it is preferable to compare both lower limbs with each other about the condition where the leg is raised, as in the balance training. In case that the measurement data of the normal lower limb is used as the reference data, in order to generate weight comparison data, joint angle comparison data and so on, one is selected from the measurement data and the reference data and the value of the selected data, which is taken half-period before the present time, is compared with the present value of the unselected data.

However, a patient with lower-limb paralysis is not likely to bend the knee or raise the leg of the paralyzed lower limb, and thus will not bend the knee or raise the leg of the paralyzed lower limb as much as the normal lower limb. Accordingly, in order to correct the abnormal walking of the patient with lower-limb paralysis to the normal walking, it is important to provide the angle-measuring parts for measuring changes in the angle of the knee joint and the hip joint.

With the use of the apparatus for lower-limb rehabilitation training of the invention, the user can take a walking training by confirming whether or not the weight load and the joint angle change show normal conditions.

As described hereinbefore, the apparatus and method for lower-limb rehabilitation training of the invention is provided to detect the weight loaded on lower limbs, measure the angle of at least one joint of the knee, ankle and hip, and analyze the usage of the paralyzed muscle of the user through the measurement data. Therefore, the invention can improve the behavior of patients with lower-limb paralysis who tend to move without using a joint, and thus the patients can take an training of moving the joint and the weight load systematically.

Furthermore, the invention can combine a game into a lower-limb rehabilitation training to stimulate the user with interest in the training, thereby inducing the user to perform repeated actions without getting bored.

In the apparatus and method for rehabilitation training of patients with lower-limb paralysis of the invention, the advantages of the invention is that the usage of paralyzed muscles was evaluated more precisely based upon the movement of the weight load and the angle of the joint and the user can correct the standing posture and train muscles necessary for walking.

Since the invention enables measurement and rehabilitation training for partial paralysis to be conducted two-dimensionally, there are advantages in that a large space or expensive equipments are not needed. Furthermore, since it can be enabled by a simple system, real-time feedback can be afforded to the user.

The invention also displays measurement and analysis results of usage of the paralyzed muscle on graphs so that the user can easily recognize the usage of the paralyzed muscle. In addition, the invention provides games using the measurement and analysis results as variables in order to stimulate the user with interest in training.

The invention can also advantageously allow the user to recognize muscles or motors, which are not unused owing to paralysis, while the user repeatedly performs the task actions so that the user can improve the usage of the paralyzed muscle.

The apparatus and method for lower limb rehabilitation training of the invention is designed for patients for partial paralysis, and as apparent in view of the purpose of the invention, can be applied to patients with paralysis in both lower limbs or those having poor balancing capability without paralysis. It should also be construed that the invention can be modified without departing from the purpose or scope of the invention.

While the present invention has been shown and described in connection with the preferred embodiments, it will be apparent to those skilled in the art that modifications and variations can be made without departing from the spirit and scope of the invention as defined by the appended claims.

What is claimed is:

1. An apparatus for lower-limb rehabilitation training of a rehabilitating lower limb, the rehabilitating lower limb of a user having a bottom, a hip joint, a knee joint and an ankle joint, the apparatus comprising:

a display for displaying a video game wherein the video game is a game of stacking a virtual brick;

a force plate for contacting the bottom of the lower limb, the force plate for measuring a value of pressure applied by the lower limb to generate measured weight data, and the force plate for being placed on a floor under the lower limb without being worn on the lower limb;

a joint angle-measuring part for measuring a joint angle value of at least one of the joints of the lower limb to generate measured joint angle data, the joint angle-measuring part including at least one goniometer adapted for being attached to said at least one joint wherein the joint angle-measuring part includes at least one selected from a group consisting of a knee joint angle-measuring part adapted for measuring an angle of the knee joint, an ankle joint angle-measuring part adapted for measuring an angle of the ankle joint and a hip joint angle-measuring part adapted for measuring an angle of the hip joint; and a controller configured to generate said video game displayed on said display, the controller being configured for controlling a directional movement of a graphical game element of the video game based on a change in said measured value of pressure and the controller being configured for controlling re-sizing of a graphical game element of the video game based on a-a change in said measured value of joint angle in such a manner that the video game requires the user to change both the force loaded on the lower limb and the joint angle of at least one of the joints of the lower limb.

2. The apparatus for lower-limb rehabilitation training of claim 1, wherein the joint angle-measuring part includes all of the knee joint angle-measuring part, the ankle joint angle-measuring part and the hip joint angle-measuring part in order to synthetically measure whether the lower limb is moved by using major muscles of the lower limb including the thigh muscles and the calf muscles and whether there is force for raising the lower limb.

3. An apparatus for lower-limb rehabilitation training of a rehabilitating lower limb, the rehabilitating lower limb of a user having a bottom, a hip, a knee and an ankle, the apparatus comprising:

a display for displaying a video game wherein the video game is a game of stacking a virtual brick;

force plate for contacting the bottom of the lower limb, the force plate for measuring a value of pressure applied by the lower limb to generate measured weight data, and the force plate for being placed on a floor under the lower limb without being worn on the lower limb;

an angle-measuring part for measuring an angle value of the lower limb to generate measured angle data, the angle-measuring part adapted for being attached to the lower limb wherein the angle-measuring part includes at least one selected from a group consisting of a knee angle-measuring part adapted for measuring an angle of the knee, an ankle angle-measuring part adapted for measuring an angle of the ankle and a hip angle-measuring part adapted for measuring an angle of the hip; and a controller configured to generate said video game displayed on said display, the controller being configured for controlling a directional movement of a graphical game element of the video game based on a change in said measured value of pressure and the controller being configured for controlling re-sizing of a graphical game element of the video game based on a change in said measured value of angle in such a manner that the video game requires the user to change both the weight loaded on the lower limb and the angle of the lower limb.

4. The apparatus for lower-limb rehabilitation training of claim 3, wherein the angle-measuring part includes all of the knee angle-measuring part, the ankle angle-measuring part and the hip angle-measuring part in order to synthetically measure whether the lower limb is moved by using major muscles of the lower limb including the thigh muscles and the calf muscles and whether there is force for raising the lower limb.

\* \* \* \* \*